(12) United States Patent
Heinz et al.

(10) Patent No.: US 6,586,039 B2
(45) Date of Patent: Jul. 1, 2003

(54) PROCESS AND APPARATUS FOR APPLYING A THERMALLY ATTACHED LUBRICATING COATING ON AN INTERIOR WALL OF A CYLINDRICAL CONTAINER FOR MEDICINAL PURPOSES

(75) Inventors: Jochen Heinz, Vendersheim (DE); Michael Spallek, Ingelheim (DE)

(73) Assignee: Schott Glas, Mainz (DE)

( * ) Notice: Subject to any disclaimer, the term of this patent is extended or adjusted under 35 U.S.C. 154(b) by 0 days.

(21) Appl. No.: 09/915,424

(22) Filed: Jul. 26, 2001

(65) Prior Publication Data

US 2002/0012741 A1 Jan. 31, 2002

(30) Foreign Application Priority Data

Jul. 28, 2000 (DE) .......................... 100 36 832

(51) Int. Cl.[7] .............................. B05D 7/22; B05D 1/32; B05D 1/40; B05D 3/06; B05D 5/08
(52) U.S. Cl. ................ 427/2.28; 427/2.1; 427/508; 427/510; 427/515; 427/230; 427/236; 427/282; 427/287; 427/348; 427/355; 427/372.2; 427/421
(58) Field of Search ................. 427/2.1, 2.28, 427/508, 515, 348, 355, 372.2, 421, 510, 230, 236, 282, 287

(56) References Cited

U.S. PATENT DOCUMENTS 3,804,663 A * 4/1974 Clark .......................... 215/12.2
4,720,521 A * 1/1988 Spielvogel et al. ......... 427/387
6,296,893 B2 * 10/2001 Heinz et al. ................ 427/2.28

FOREIGN PATENT DOCUMENTS

| DE | 197 53 766 A | 6/1999 | |
| DE | 19 7 53 766 A1 * | 6/1999 | ............... C08J/7/18 |
| EP | 0 597 613 A1 * | 5/1994 | ........... C08L/83/04 |
| EP | 0 675 315 A | 10/1995 | |
| EP | 0 675 315 A1 * | 10/1995 | ............. F16N/7/32 |

OTHER PUBLICATIONS

D. Stoye, W. Freitag: Paints, Coatings and Solvents, Wiley–VCH Verlag GMBH, Weinheim 1998, p. 217.

* cited by examiner

*Primary Examiner*—Shrive P. Beck
*Assistant Examiner*—Jennifer Kolb Michener
(74) *Attorney, Agent, or Firm*—Michael J. Striker

(57) ABSTRACT

The process for applying a thermally attached lubricating coating on an interior wall of a cylindrical medicinal container includes applying a thermally attachable lubricant to an interior wall of the container; uniformly spreading or homogenizing the applied lubricant on the wall to form a lubricating coating and thermally attaching the lubricating coating by irradiating the lubricating coating with infrared radiation selectively in a cylindrical region of the container at elevated temperatures above a maximum operating temperature of the container. The apparatus for performing the process includes an insertable spraying device for applying the thermally attachable lubricant (3) to the interior wall of the container (1) from a supply reservoir; a device for homogenizing the lubricant to form the lubricating coating (4) and a rod-shaped infrared radiation source (5) insertable into an interior space of the container. The radiation source has a radiation screen (5a, 6, 7) for keeping the radiation away from the container outlet.

8 Claims, 3 Drawing Sheets

A

B

PROCESS AND APPARATUS FOR APPLYING A THERMALLY ATTACHED LUBRICATING COATING ON AN INTERIOR WALL OF A CYLINDRICAL CONTAINER FOR MEDICINAL PURPOSES

BACKGROUND OF THE INVENTION

1. Field of the Invention

The present invention relates to a process for applying a thermally attached lubricating coating to the interior wall of a cylindrical medicinal container, which has a tapered outlet on one end and a slidable elastomeric stopper acting as a plunger or piston at the other end of the container. The invention also relates to an apparatus for performing this process.

2. Related Art

Containers for medicinal purposes, especially pharmaceutical containers or containers for diagnostic purposes, have slidable elastomeric closure devices, such as pistons or piston stoppers. The slidable elastomeric closure device for these containers is inserted in an interior chamber in a hollow body of the container and slides lubricated on an interior wall of the hollow body. Syringe cylinders of fillable syringes, injector bodies of cylindrical ampoules and containers are typical examples. However other examples include the piston burettes used in analytical chemistry. In order to solve this problem correctly a silicone-lubricating coating is often applied to the interior wall of the hollow body.

The fillable syringes are of special significance here. Fillable syringes made from glass have been disclosed and are known from many years from numerous publications. These fillable syringes comprise glass, which does not have an integrated needle. Glass syringes with attached needles are notoriously well known.

This sort of fillable syringe made from glass requires a lubricant between the movable elastomeric piston or plunger and the glass syringe cylinder. Silicone oil is preferred for this purpose. This silicone oil is usually applied by washing the interior of the injector cylinder. Great differences exist between the processing syringe bodies with and without needles. Since the needle is usually attached with glue, such as epoxy resin, or other adhesives, that have limited heat resistance different process conditions are required.

A maximum processing temperature of 130° C. is allowed at the site of the glue or adhesives in finished syringes with hollow needles attached with an adhesive or glue. An adherent lubricant coating is only guaranteed however, when the lubricant, preferably silicone, is applied at temperatures of about 300° C.

Thus it is known to provide a glass syringe cylinder with a silicone coating at about 300° C. and then subsequently to connect a needle-supporting piece with the syringe body that is made from glass. However this method requires additional assembly effort and thus additional costs, which make it considerably disadvantageous, because it is a mass-produced product.

If a silicone lubricant coating is applied to a syringe with a needle already attached to it, there is a risk that the often very narrow needle duct is filled with silicone lubricant, which can lead easily to unintended injection of silicone oil in application.

This problem also exists in pre-filled plastic syringes. DE 197 53 766 A1 describes a method for providing containers for medicinal purposes with an interior silicon coating. These containers comprise an elongated plastic hollow body, especially a syringe cylinder. The silicone coating is provided by special reactive silicone oil, which hardens under the influence of light. This method avoids the otherwise conventional step of pre-conditioning the interior surface, e.g. by plasma treatment.

SUMMARY OF THE INVENTION

It is an object of the present invention to provide a process of the above-described type for providing a thermally attached lubricating coating on an interior wall of a cylindrical medicinal container, which has a tapered outlet at one end and an elastomeric stopper at the other end, which is slidable like a piston in the container, which process is conducted, so that a thermal bonding of the lubricant to the interior wall is possible at very high temperatures without damage to temperature sensitive parts at the outlet end of the container.

It is another object of the present invention to provide an apparatus for performing the improved process according to the invention.

According to the invention this process comprises the steps of:

a) applying a thermally attachable lubricant to the interior wall of the container in a known manner;

b) homogenizing the applied lubricant on the interior wall to form a lubricating coating; and c) thermally attaching the lubricating coating by irradiating the lubricating coating with infrared radiation selectively in a cylindrical region of the container at elevated temperatures above a maximum operating temperature of the container.

The apparatus for performing this process according to the invention comprises means for applying the thermally attachable lubricant from a supply reservoir to the interior wall of the container;

means for homogenizing the lubricant applied by the means for applying to form the lubricating coating; and a rod-shaped infrared radiation source insertable into an interior space in the container, said radiation source having a radiation screen or barrier for keeping the radiation away from the container outlet.

By means of selective heating of the container wall with the infrared radiation the lubricating coating or layer applied to it can be reliably attached in a simple manner and at a high temperatures, while the outlet of the container remains free of lubricant and the attachment of the syringe or injector needle is not damaged. At the same time the germ count and the endotoxins are reduced because of the high temperatures. Furthermore the method according to the invention does not require pre-conditioning of the surface to which the lubricant is applied, e.g. by plasma treatment.

The method according to the invention and the apparatus for performing that method are thus advantageous for applying a thermally attached lubricating coating, especially a silicone coating, both to glass or plastic syringe bodies with integral needles and without integral needles.

Preferably the silicone oil used as the lubricant in the method according to the invention should be reactive silicone oil, non-reactive silicone oil or a mixture of both types of silicone oil. Other thermally fixable or attachable lubricants can be used.

According to a preferred embodiment of the invention the lubricant is applied by spraying, which leads to a relatively uniformly wetting silicone coating in a very simple manner. However other known methods for applying lubricants, especially silicone oils, are also conceivable.

The temperature range for the thermal attachment, among other things, depends on whether or not a glass or a plastic container is to be coated. The temperature range is preferably at about 300° C. in the case of glass containers.

For plastic containers the thermal attachment should be performed in a temperature range, which is about 50° C. above the maximum operating temperature of the plastic container.

For selective irradiation of the interior wall of the container the rod-shaped infrared radiation source has a preferably top-side covering member in the form of a cylindrical cap acting as a radiation screen or shield. Alternatively the screen can be a mushroom-shaped body, which is attached with its stem to the top end of the radiation source and which keeps the infrared radiation away from the outlet of the container. Other forms of the screen or shield are conceivable.

BRIEF DESCRIPTION OF THE DRAWING

The objects, features and advantages of the invention will now be illustrated in more detail with the aid of the following description of the preferred embodiments, with reference to the accompanying figures in which.

DETAILED DESCRIPTION OF THE PREFERRED EMBODIMENTS

Figure 1:
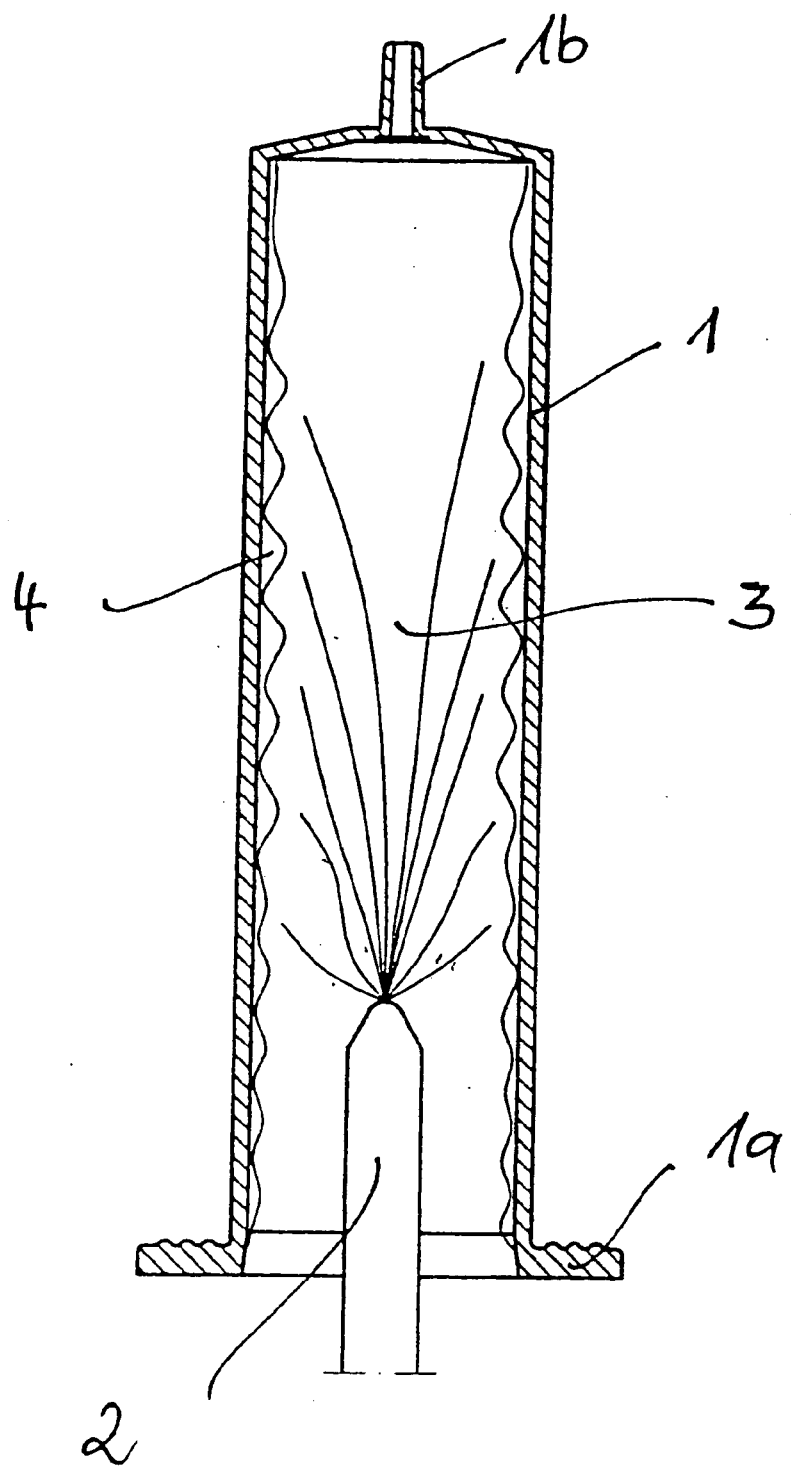
FIG. 1 is a schematic longitudinal cross-sectional view showing the application of a lubricant to the interior walls of a syringe body by spraying in the method according to the invention.

FIG. 1 shows a glass or plastic syringe body with a molded gripping element 1a and a Luer-cone 1b at the outlet. A spraying nozzle 2 is inserted in the syringe body 1. The conventional silicone emulsion or a reactive thermally attachable silicone 3 is sprayed on the interior surface of the syringe body 1 to be coated by means for the spraying nozzle 2. Silicone oil mixtures of different types may also be sprayed by the spraying nozzle 2.

The spraying according to FIG. 1 is only one of the possibilities. The silicone oil emulsion or reactive silicone oil can also be applied by a sponge or by means of a movable piston, which has a suitable outlet, or by other known methods, such as brushes.

In the next step in the method according to the invention the still unattached lubricant film 4, is distributed as uniformly as possible (i.e. by definition here homogenizing) on the inner surface of the syringe body 1 by a wiping device or squeegee on a suitable tool.

After the homogenizing step the still movable lubricant film 4 is attached to the surface by selective heat treatment. This heat treatment occurs according to FIG. 2 by insertion of a rod-shaped infrared radiation source 5, e.g. a Nernst rod, or the like, into the interior of the syringe body 1, whereby the inner surface of the entire syringe body 1 is heated to temperatures above a maximum operating temperature of the syringe body and thus the lubricant film 4 is attached to the interior wall of the syringe body 1.

The head or top geometry of the infrared radiation source is selected so that only a minimum amount of radiation is propagated in the direction of the syringe head with the Luer-cone 1b or a hollow needle and the glue attaching it to the syringe head (not shown).

Figure 2:
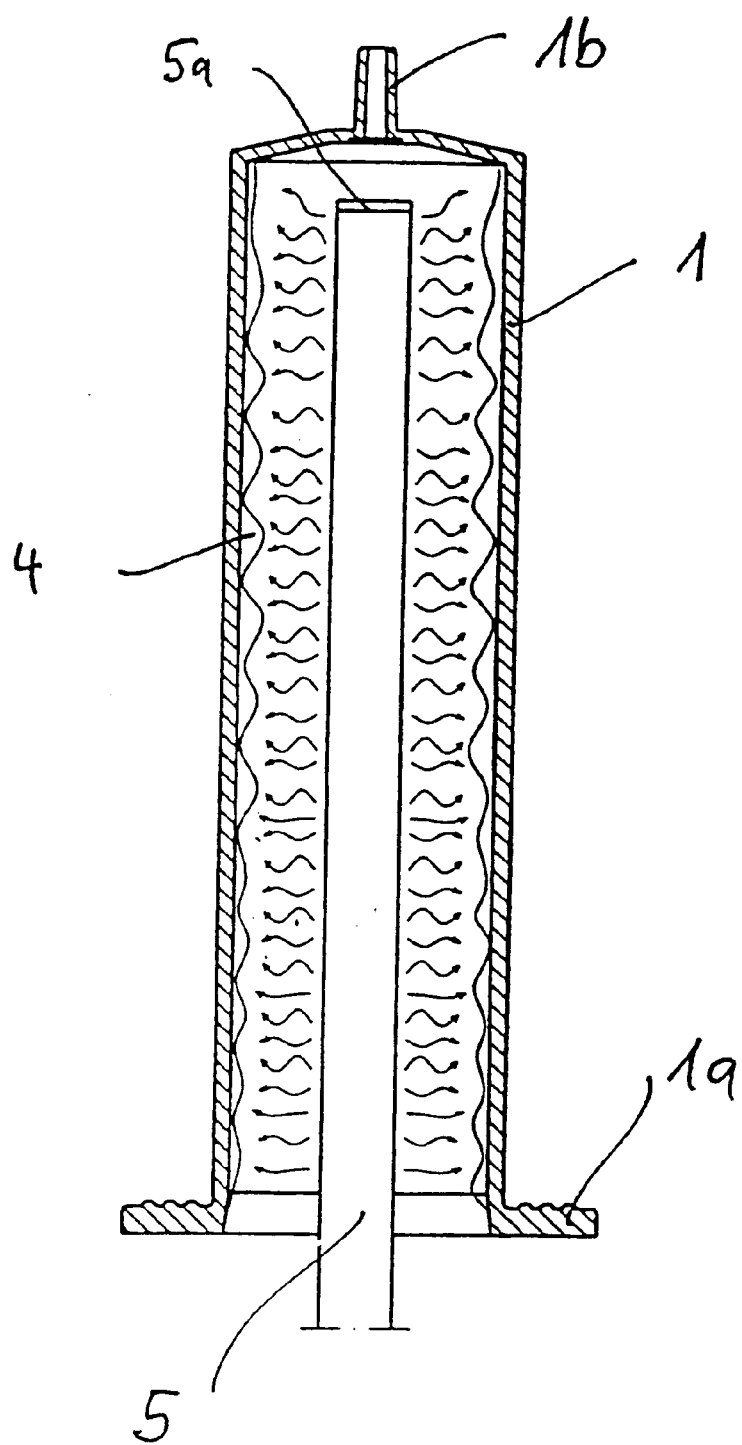
FIG. 2 is a schematic longitudinal cross-sectional view showing the thermal attachment of the lubricant applied in the step shown in FIG. 1 and its homogenizing by means of a rod-shaped infrared source, which is inserted in the interior of the syringe body.
Figure 3:
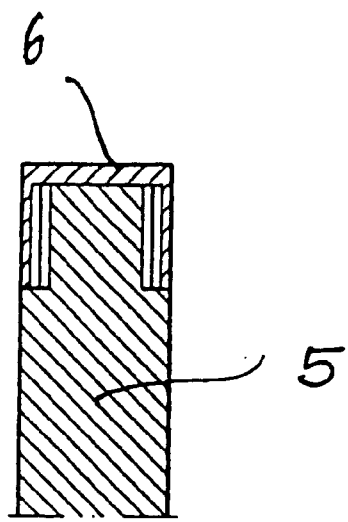
FIGS. 3A and 3B are respective detailed cross-sectional views through a top end of the rod-shaped infrared source according to FIG. 2 showing different embodiments for a shield or screen for preventing infrared radiation from reaching the outlet of the syringe body. The shield or screen in the embodiment of FIG. 3A is a cylindrical covering cap. In the embodiment of FIG. 3B it is a mushroom-shaped body, which is connected with the top end of the radiation source with its stem.
Figure 3:
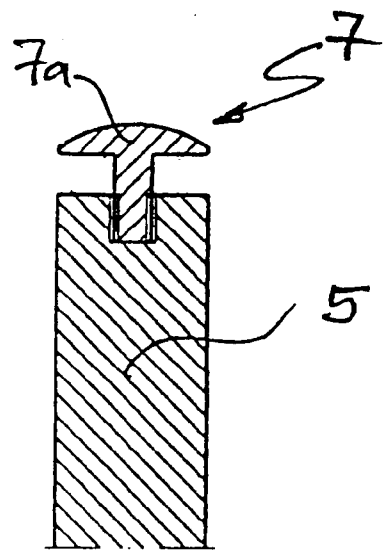

In FIG. 2 this head geometry is symbolically indicated by the head end covering disk 5a. FIGS. 3A and 3B show two different embodiments for the top or head end structure of the rod-shaped infrared radiation source 5. In FIG. 3A a cylindrical covering cap 6 made of heat-resistant material is screwed on the head or top of the infrared radiation source 5, while in FIG. 3B a mushroom-shaped body 7 is screwed on the top end of the infrared radiation source 5. The screen part 7a of the mushroom-shaped body 7 keeps the infrared radiation away from the syringe head.

A thermally attached lubricant coating, for example of silicone oil, can be provided on the cylindrical part of the injector body 1 without hardening silicone oil in the needle duct or channel and thus clogging it by means of the head structure of the infrared radiation source.

Attachment temperatures of about 300° C. can be provided during coating of glass syringe bodies with glued-on needles without damage to the site where the glue is located. Significant reduction of the germ count and reduction of endtoxins are examples of additional advantages.

The attachment temperatures for plastic syringe bodies can be about 50° C. above the maximum operating temperature of the plastic syringe body during attachment of the lubricating coating to the plastic syringe body with or without integrated needle. A surface activation occurs (in situ) at the same time as the heating to attach or bond the lubricant to the interior surface of the syringe body, which advantageously affects the adherence of the lubricating film.

The lubricant preferably comprises a silicone oil emulsion, a reactive silicone oil or mixtures thereof according to the above-mentioned reference DE 197 53 766 A1.

Reactive silicone oils contain reactive functional groups in contrast to non-reactive silicone oils, which permit cross-linking among themselves and also with other surfaces.

The reactive silicone oil is a siloxane molecule, which contains functional groups for hardening mechanisms in accordance with its purpose or function. A reactive silicone oil contains especially vinyl groups, which cross-link under the influence of temperature and UV radiation. The cross-linking reaction is catalyzed especially by platinum compounds.

With a mixture of reactive and non-reactive silicone oil the hardened silicone oil then forms a solid film, which functions as a separate coating between the injector body and the piston stopper. Jamming of the stopper, especially when it is made of butyl rubber, on the surface of the syringe body is prevented because of this attached lubricating film. The non-reactive silicone oil, dimethylpolysiloxane, is mixed with reactive silicone oil to reduce sliding friction. In this latter embodiment the reactive portion of the silicone oil forms the adherent base coating after cross-linking, in which the non-reactive silicone oil is embedded and the effects the lubricating power.

The composition of the silicone agent based on reactive silicone oils comprises vinyl-group-containing silicone oils, cross-linking agents, catalysts, solvents and non-reactive dimethylpolysilixoane.

The viscosity of the reactive silicone oil is in a range of from 10,000 to 100,000 mm$^2$/s for a one component system or from 200 to 5000 mm$^2$/s for a multi-component system. The viscosity of the non-reactive silicone oils is in the range of from 350 to 20,000 mm$^2$/s.

The silicone oils however can be diluted for application, especially when the application is by spraying.

The thickness of the silicone lubricant coating is in a range of from 10 nm to 1 $\mu$m.

The silicone oils can comprise the following silicone compounds:

Non-cross linked polar silicones or polysilioxanes, especially non-reactive polydimethyldisiloxanes (PDMS) or reactive polymeric siloxanes, copolymers of alkylamine-modified methoxysiloxanes, polysiloxanes with aminoalkyl groups.

The cross-linking occurs with known methods, especially with UV light or by plasma polymerization.

The disclosure in German Patent Application 100 36 832.8-45 of Jul. 28, 2000 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in a process for applying a thermally attached lubricating coating on an interior wall of a cylindrical medicinal container and an apparatus for performing this method, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A process for applying a thermally attached lubricating coating on an interior wall of a cylindrical region of a medicinal container, said medicinal container having a tapering outlet connected to one end of the cylindrical region, said process comprising the steps of:
    a) applying a thermally attachable lubricant to the interior wall of the cylindrical region;
    b) homogenizing the lubricant applied in step a) to the interior wall of the cylindrical region in order to form a lubricating coating; and
    c) thermally attaching the lubricating coating to the interior wall of the cylindrical region by selectively irradiating the lubricating coating in the cylindrical region with infrared radiation at an elevated temperature above a maximum operating temperature of the container.

2. The process as defined in claim 1, wherein said lubricant is silicone oil.

3. The process as defined in claim 2, wherein said silicone oil is a non-reactive silicone oil, a reactive silicone oil or a mixture of said reactive silicone oil and said non-reactive silicone oil.

4. The process as defined in claim 1, wherein the applying of the lubricant to the interior wall of the container takes place by spraying.

5. The process as defined in claim 1, wherein said container is a glass container and said elevated temperature at which the thermally attaching of the lubricating coating occurs is about 300° C.

6. The process as defined in claim 1, wherein said container is a plastic container and said elevated temperature at which the thermally attaching of the lubricating coating occurs is about 50° C. above said maximum operating temperature of said container.

7. The process as defined in claim 1, wherein the thermally attachable lubricant is not applied to the tapering outlet and no thermally attachable lubricant is attached or bonded to the tapering outlet.

8. The process as defined in claim 1, further comprising at least partially shielding the tapering outlet from said infrared radiation so as to protect said tapering outlet from heating by said infrared radiation and so that no thermally attachable lubricant is attached or bonded to the tapering outlet.

* * * * *